United States Patent [19]

Duembgen et al.

[11] 3,932,500

[45] Jan. 13, 1976

[54] RECOVERING ANHYDROUS ACRYLIC ACID

[75] Inventors: Gerd Duembgen, Dannstadt; Heinz Engelbach, Limburgerhof; Walter Frey, Mannheim; Richard Krabetz, Kirchheim; Ulrich Lebert, Ludwigshafen; Hermann Spitzl, Ludwigshafen; Fritz Thiessen, Ludwigshafen; Carl-Heinz Willersinn, Ludwigshafen, all of Germany

[73] Assignee: Badische Anilin- & Soda-Fabrik Aktiengesellschaft, Ludwigshafen (Rhine), Germany

[22] Filed: July 17, 1972

[21] Appl. No.: 272,551

[30] Foreign Application Priority Data

July 21, 1971 Germany.............................. 2136396

[52] U.S. Cl.................. 260/526 N; 203/63; 203/68; 260/530 N; 260/533 N
[51] Int. Cl.².................C07C 53/00; C07C 55/00; C07C 57/00; C07C 59/00
[58] Field of Search........ 260/526 N, 530 N, 533 N; 203/15, 51, 55, 62; 55/68, 69

[56] References Cited
UNITED STATES PATENTS

| | | | |
|---|---|---|---|
| 2,575,285 | 11/1951 | Carlson et al. | 203/69 |
| 3,405,172 | 10/1968 | Brown | 260/530 N |
| 3,432,401 | 3/1969 | Tcherkawsky | 260/526 N |
| 3,433,831 | 3/1969 | Yomiyama | 260/526 N |
| 3,507,915 | 4/1970 | Newman | 260/526 N |
| 3,513,632 | 5/1970 | Hess et al. | 260/533 N |
| 3,657,332 | 4/1972 | Sennewald | 260/526 N |

*Primary Examiner*—Norman Yudkoff
*Assistant Examiner*—Frank Sever
*Attorney, Agent, or Firm*—Johnston, Keil, Thompson & Shurtleff

[57] ABSTRACT

Acrylic acid practically devoid of water, acrolein, formaldehyde and acetic acid is obtained at particularly low cost by countercurrent scrubbing and quenching of the reaction gas formed in the catalytic oxidation of propylene and/or acrolein with a high-boiling extremely hydrophobic solvent followed by processing of the extract.

6 Claims, 1 Drawing Figure

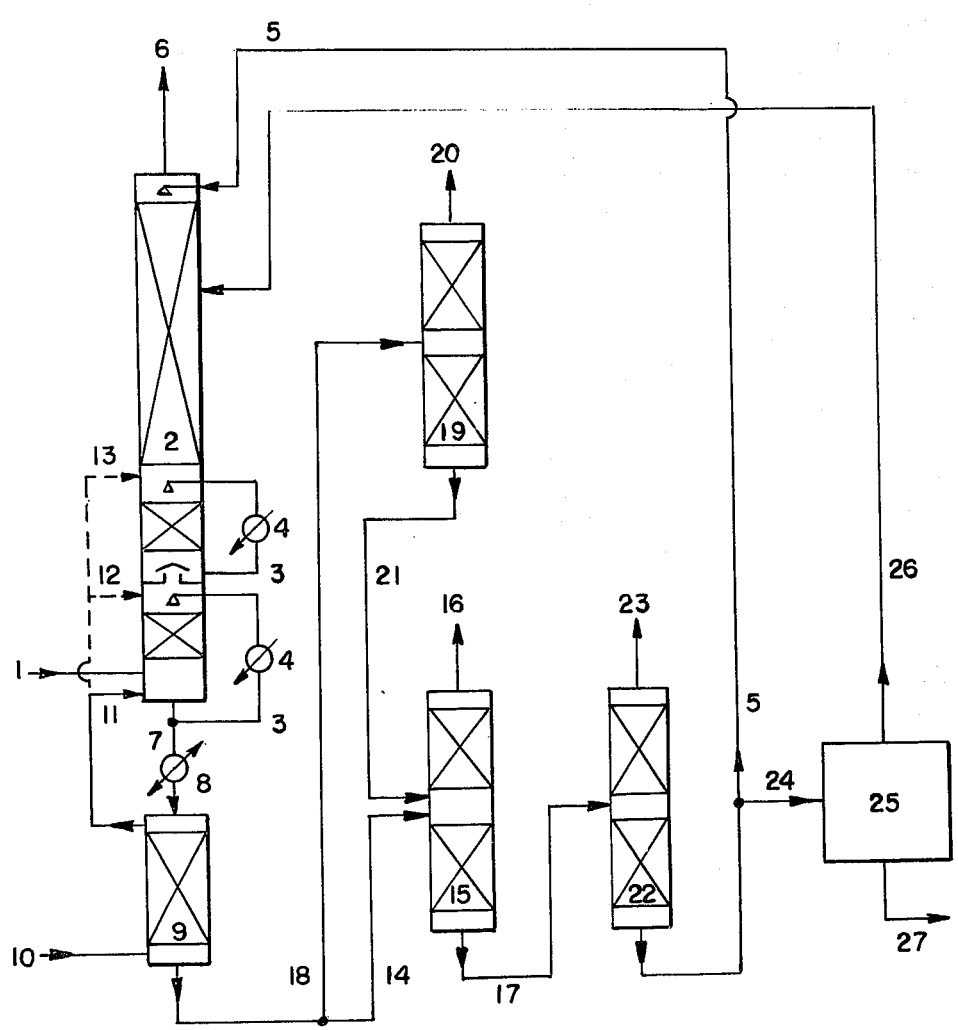

RECOVERING ANHYDROUS ACRYLIC ACID

The invention relates to a process for the recovery of anhydrous acrylic acid from reaction offgas such as is obtained in the oxidation of propylene and/or acrolein.

In addition to the Reppe synthesis, a process for the production of acrylic acid which is of current interest is the gas phase oxidation of propylene or acrolein. Oxidation of propylene and/or acrolein is carried out with oxygen or a gas containing oxygen in the presence of a catalyst (for example an oxide of the elements molybdenum, chromium, vanadium or tellurium) at elevated temperature. For safety reasons and for better control of the heat of reaction evolved the mixtures of the reactants are diluted with inert gas or steam. After the reaction there is consequently formed a gaseous reaction mixture which (in addition to unreacted propylene and/or acrolein) contains, inter alia, the desired acrylic acid but also varying amounts of water vapor, oxides of carbon, nitrogen, oxygen, acetic acid, formaldehyde and maleic anhydride. The economics of the process are largely dependent on how the acrylic acid is recovered from the gas mixture and purified, particularly on how the water is separated. Various methods of doing this are known from the literature.

U.K. Pat. Specifications Nos. 948,687 and 953,763 disclose, inter alia, the recovery of aqueous acrylic acid solutions by indirect cooling of the reaction gas (quenching). Similar methods are described in German Patent Specification No. . . DT-OS-1568925 (Pat. application K 59 985 IVb/120). A considerable disadvantage of these methods is that the acrylic acid obtained as a dilute aqueous solution of not more than 45% strength. The content of acrolein, acetic acid and formaldehyde in this solution is another disadvantageous phenomenon. The separation of these substantially liquid components requires considerable expense for distillative and/or extractive purification of the acrylic acid.

The teaching of German Published Specification No. 1,568,937 represents a certain advance because some of the said disadvantages can be avoided. In this method the hot reaction gas formed in the oxidation of propylene or acrolein, which is at a temperature of from 300° to 600°C, is first cooled, without condensation, to a temperature of from 90° to 200°C, preferably from about 100° to 170°C, and then extracted countercurrently with an ester of an aliphatic or aromatic monocarboxylic or dicarboxylic acid whose alcoholic component contains from one to eight carbon atoms and whose acid component contains from five to twenty carbon atoms, or with tributyl or tricresyl phosphate at a temperature of from 30° to 100°C at a pressure of from 0.5 to 5 atmospheres absolute, preferably at atmospheric pressure, the ester being used in such an amount that the content of acrylic acid in the extract obtained is from about 5 to 35% by weight, preferably from 10 to 25% by weight, acrylic acid being distilled off from the resultant extract in the form of a concentrated aqueous solution of for example 70% by weight strength and the distillation residue being reused for extraction of reaction gas containing acrylic acid. A preferred embodiment of this process consists in expelling acrolein from the extract containing acrylic acid at elevated temperature, preferably at about 100° to 140°C prior to distillation and combining the acrolein vapor with the constituents of the reaction gas which have not been absorbed by the extractant and which consist mainly of steam together with unreacted propylene and/or acrolein, formaldehyde, carbon monoxide, carbon dioxide and nitrogen. Then excess water of reaction and formaldehyde are partly condensed out from the resultant gas mixture by cooling to about 20° to 70°C and the residual gas is supplied again to the oxidation process together with fresh propylene and/or acrolein.

The advantage of the said process consists in the fact that a highly concentrated aqueous acrylic acid of a strength of about 70% by weight can be recovered and that this contains only traces of formaldehyde (in the Examples about 0.1% and less than 1% by weight). As before however a separate process step is necessary to separate the water and also the acetic acid from the acrylic acid.

The object of the present invention is to provide a process for the recovery of an acrylic acid which will be devoid of water, acrolein, formaldehyde and acetic acid.

This object is achieved by a process for the recovery of anhydrous acrylic acid, obtained by catalytic oxidation of propylene and/or acrolein, by countercurrent scrubbing of the reaction gas with a high-boiling inert organic solvent, which comprises carrying out the countercurrent scrubbing with an extremely hydrophobic solvent and processing the resultant mixture of solvent and acrylic acid by a conventional method.

The process of the invention is carried out by scrubbing the reaction gas countercurrently (while avoiding the formation of an aqueous phase) with a high-boiling extremely hydrophobic solvent, for example a solvent from the group of aliphatic or aromatic hydrocarbons or ethers or mixtures of the same, in an absorption column and treating the resultant mixture of hydrophobic solvent and acrylic acid in order to separate them from the other specified components by a conventional method. Such a treatment may be effected for example in a desorber in which the mixture of solvent and acrylic acid is treated countercurrently with a stripping gas, the desorber gas being returned to the absorber and, if desired, acetic acid and acrylic acid devoid of water, acrolein and formaldehyde being distilled off from the desorber discharge and the solvent or solvent mixture being used again for the absorption after maleic anhydride and ester-like oligomeric acrylic acids have been separated.

In the process according to the invention, pressure and temperature have to be chosen in dependence on the water content of the reaction gas in order to avoid the occurrence of an aqueous phase in the absorption. It is advantageous to maintain the lowest possible temperature in absorption because the said extremely nonpolar solvents do not have very good solvent power for acrylic acid. In other words, if too high a temperature is chosen, some acrylic acid may be lost as a result of it escaping at the top of the absorber together with the water.

Depending on the water vapor content of the reaction gas, the favorable absorption temperature at standard pressure is from about 30° to 80°C. This range is of course displaced if other pressures are used for the absorption.

Extremely non-polar hydrophobic organic solvents which are to be used according to the present invention are those which do not contain any outwardly acting polar groups which would be capable for example of forming hydrogen bridge bonds. They are mainly inert fractions such as the middle oil fractions of paraffin distillation, but also ethers providing their groups attached to the oxygen atoms are bulky and sufficiently large to screen off the free electron pairs of the oxygen, for example diphenyl ether, diphenyl and preferentially mixtures of diphenyl and diphenyl ether, known as "diphyl". A particularly preferred representative of the organic solvents to be used in accordance with the invention is a mixture of 75% of diphenyl ether and 25% of diphenyl.

It has proved to be advantageous to use, as the inert extremely hydrophobic compounds, hydrocarbons or ethers or mixtures of the same known as heat transfer oils whose boiling point at standard pressure is above 170°C and whose viscosity at temperatures within the range from 30° to 80°C is less than 10 centistokes, preferably less than 3 centistokes.

The solvent is used in such an amount that the absorber discharge contains up to about 10% by weight of acrylic acid. The maximum content achievable depends on, inter alia, the absorption temperature, the size of the column and the desired absorption yield.

The absorber discharge contains not more than 5% by weight of water and traces of acrolein and formaldehyde as well as small amounts of acetic acid.

The residual water and the small amounts of acrolein and formaldehyde are then removed by conventional working methods. This is preferably carried out in a desorber in which the said impurities are expelled from the solvent containing acrylic acid in countercurrent with a stripping gas, for example nitrogen or air. The amount of stripping gas required depends mainly on the desorption temperature which is advantageously from 20° to 50°C above the absorption temperature at the same pressure. In this case the amount of stripping gas is from 5 to 25% by volume of the amount of reaction gas in order to obtain practically anhydrous acrylic acid in the solvent. The desorber offgas is passed into the absorber column so that acrylic acid vapor entrained therein can be subjected again to countercurrent extraction.

It is an advantage of this process that a more or less large proportion of the acetic acid in the absorber can be withdrawn at the top depending on the conditions chosen. It is even possible to separate the acetic acid almost completely from the acrylic acid by combining absorption with the desorption described in the preceding paragraph.

Processing of the desorber discharge depends to some extent on whether it still contains acetic acid or not. If the acetic acid has already been removed in the absorption and desorption, pure acrylic acid can be immediately distilled off from the solvent. If acetic acid is still present up to a few percent, it has to be distilled off from the mixture prior to recovering the acrylic acid. This is more advantageous than a common separation of acetic acid and acrylic acid followed by separation of the two acids by distillation because the relative volatilities are favorably influenced by the presence of the solvent, and the presence of pure acrylic acid at too high a temperature can be avoided.

After the acrylic acid has been separated from the solvent it is preferred to remove maleic anhydride prior to reuse for absorption, in order to avoid concentration in the recycled solvent. If a solvent having a sufficiently high boiling point (about 220°C) is used, the maleic anhydride may be distilled off in a column. Another way to separate maleic anhydride independently of the boiling point of the solvent is to carry out a liquid-liquid extraction with water; in this way it is possible without difficulty to recover practically the whole of the maleic anhydride as an aqueous concentrated maleic acid solution in one extraction stage.

In all methods of working up acrylic acid, ester-like oligomeric acrylic acids are formed. In the present process an accumulation in the solvent can be avoided by subjecting the solvent to a thermal treatment at a temperature above 180°C prior to resuse so that the oligomers are cracked. If the acrylic acid formed is allowed to distil over, practically complete cracking is achieved for example within 20 minutes at 230°C.

To avoid accumulation it is of course also possible to free only branch streams of the solvent from maleic anhydride and esterlike oligomers.

As is conventionally done, stabilizers for acrylic acid are added in all processing methods. A branch stream of the solvent has to be purified by evaporation to avoid accumulation of these additives and other practically non-vaporizable substances, for example polymerized non-ester-like acrylic acids, in the solvent in the abovementioned method. This step of evaporation may advantageously be combined with the cracking of the ester-like oligomeric acrylic acids.

The process will now be described in greater detail in a special embodiment with reference to the accompanying drawing:

Hot reaction gas (at from 200° to 300°C) coming from the oxidation stage in the oxidation of acrolein and/or propylene and containing not only acrylic acid but also inter alia water vapor, acrolein, formaldehyde, acetic acid, maleic anhydride and, as mentioned above, inert gas, is fed through line 1 to an absorber column 2 in which the reaction gas is first quenched to the temperature desired in aborption by means of one or more than one circulation system 3 and cooler 4, by direct use of a solvent. The solvent is supplied through line 5 to the top of the absorber column 2 which may for example be packed or fitted with trays and this scrubs out, inter alia, acrylic acid from the reaction gas in countercurrent. The unabsorbed constituents of the reaction gas with traces of solvent leave the absorber column through line 6. The offgas coming from this absorber may be further treated, for example by subsequent cooling, to recover the solvent traces and constituents from the reaction gas. The liquid discharge from the absorber column 2, which contains mainly acrylic acid, solvent and the constituents described above, is passed through line 7, if necessary with cooling or heating in a heat exchanger 8, to the top of a desorber column 9, which may for example be a packed column or a tray column. Stripping gas is blown in countercurrent to the descending liquid through line 10. The desorber offgas (the used stripping gas) is passed through line 11, and if desired through line 12 or 13, into the absorber column 2. In this stripping, water, acrolein and formaldehyde in the absorber discharge are removed practically completely. Acetic acid may also be expelled in this operation, as has been mentioned above.

The liquid discharge from the desorber column 9 is supplied through line 14 to a distillation column 15, which may be for example be a bubble tray column. Pure acrylic acid is drawn off through line 16 at the top of the distillation column 15. If acetic acid is still contained in the liquid discharge from the desorber column 9, this discharge is first supplied through line 18 to a distillation column 19, which may be for example a bubble tray column, freed therein from acetic acid (removed through line 20) and only then passed through line 21 to the distillation column 15.

The liquid discharge from the column 15 is supplied through line 17 to a distillation column 22, which may be for example a tray column, and is freed therein from maleic anhydride (removed through line 23). The major portion of the solvent from the bottoms of the column 22 is returned through line 5 to the top of the absorber column 2. A branch stream is passed through line 24 to solvent purification 25, which may consist for example of a circulation evaporator, in which the solvent is distilled off, with simultaneous cracking of the ester-like oligomeric acrylic acids, and separated from residues which are removed through line 27. The distilled solvent containing acrylic acid is returned for example through line 26 to the middle of the absorber column 2.

The process according to this invention, including the preferred embodiment, shows a number of decisive advantages over the prior art methods. An extract containing acrylic acid which is practically free from water, acrolein and formaldehyde is obtained by the use of an extremely hydrophobic solvent and the processing methods (known per se) especially in the desorption stage. It is even possible to obtain the solvent containing acrylic acid substantially free from acetic acid so that pure acrylic acid may be recovered from the solvent by distillation. It is moreover important that the solvents used are substances which are extremely stable both thermally and chemically. Because of the thermal stability, for example hot reaction gas at more than 200°C from the oxidation may be brought directly into contact with the solvent without any precooling, in contrast to the prior art. It is impossible with high boiling point esters as used in the prior art to maintain such high temperatures because thermal cracking is already possible in the case of the esters. Moreover, the new process is very economical.

The following Examples illustrate the invention.

EXAMPLE 1

(with reference to the drawing)

2692 liters (STP) of reaction gas (which contains 2.52% by volume of acrylic acid, 0.168% by volume of acetic acid, 0.25% by volume of formaldehyde, 0.07% by volume of acrolein, 10.2% by volume of water vapor, 0.115% by volume of maleic anhydride, the remainder being inert substances such as nitrogen, carbon dioxide, carbon monoxide, propylene and the like) passes at a temperature of about 220°C into the lower portion of an absorption column 2, which consists of a total of thirty-four bubble cap trays and two circulation systems for withdrawal of heat. A mixture of 75% of diphenyl ether and 25% of diphenyl is supplied at a temperature of from 50° to 53°C at the rate of 1.98 kg/hour through line 5 to the top of the countercurrent absorption column 2 as the high boiling point non-polar solvent. This solvent is stabilized with phenothiazine to prevent polymerization of acrylic acid. The reaction gas is cooled to 50° to 60°C in the lower portion of the absorber column by circulating the solution through a heat exchanger 4. Absorption heat evolved in this stage is also removed in this way. This process is repeated in the second absorption stage for further removal of absorption heat. The absorber discharge contains less than 5% of water based on 100% acrylic acid. The absorber discharge 7 is brought to a temperature of from 95° and 100°C by heat exchanger 8 and fed to the top of the desorber column 9 which contains a total of eighteen bubble cap trays. 360 liters (STP) per hour of stripping gas (nitrogen or air) is fed into the desorber column through line 10. The stripping gas removes all of the water and most of the acetic acid from the solution. The stripping gas is then returned through line 13 into the absorber column in which substantially only the acrylic acid entrained with the stripping gas is absorbed again.

The offgas leaving the absorber column 2 through line 6 is cooled to a temperature of about 15°C so that the solvent entrained from the absorber column according to its partial pressure is separated from the condensed water and returned to the solvent loop. The offgas 6 contains practically all substances having a lower boiling point than acrylic acid, including acrolein, formaldehyde and water. Loss of acrylic acid in the offgas is about 1%.

The desorber discharge passes into the acrylic acid column 15, in which all volatile substances down to and including acrylic acid are drawn off in vacuo through line 16, an about 99% acrylic acid with 0.5% of acetic acid and about 0.1% of water being obtained. The bottoms is passed into the maleic anhydride column 22 for removal of maleic anhydride, and here maleic anhydride is withdrawn in vacuo over the top 23. After the solvent has been cooled to 50° to 53°C it is returned through line 5 to the top of the absorber column, thereby completing the cycle. In a branch stream a fraction of about 5% of the solvent is withdrawn through line 24 and subjected to solvent purification at 25. In this solvent purification unit the solvent is distilled over the top at a temperature of 258°C and at the same time the diacrylic acid contained therein in a very small amount is practically completely cracked and distilled as acrylic acid over the top with the solvent. The distillate is returned through line 26 into the absorber column 2.

EXAMPLE 2

The reaction gas has the same composition as in Example 1 except that the water content is 15.0% by volume. The process is carried out in a way similar to that described in Example 1. 2.5 kg/hour of solvent (a mixture of 75% of diphenyl ether and 25% of diphenyl) is supplied at a temperature of 58°C to the top of the countercurrent absorption column 5. Further processing is as described in Example 1, only the desorber temperature is raised slightly to 100° to 105°C. The product is an about 99% acrylic acid with about 0.7% of acetic acid and 0.1% of water. The loss of acrylic acid is 1% of acrylic acid (in the offgas).

EXAMPLE 3

The composition of the reaction gas is the same as in Example 1 except that the acetic acid content is 0.3% by volume. The process is carried out in a way similar to that described in Example 1. 2.5 kg/hour of solvent (mixture of 75% of diphenyl ether and 25% of diphenyl) is supplied at a temperature of from 50° to 53°C to the top of the countercurrent absorption column 5. The desorber temperature is lowered as compared with Example 1 to 75° to 80°C. The amount of stripping gas supplied through line 10 is 250 liters (STP) per hour. The desorber discharge passes through line 18 into the acetic acid column 19 in which 11 g of acetic acid and 1 g of water are withdrawn over the top. The bottoms contains the acrylic acid (devoid of acetic acid and water) in solution and it is fed through line 21 into the acrylic acid column 15. A more than 99% acrylic acid is withdrawn here practically completely. About 0.5 to 1% of acrylic acid and about 10.5 g of acetic acid are contained in the offgas (line 6). Otherwise the procedure described in Example 1 is followed.

We claim:

1. A continuous process for recovering anhydrous acrylic acid from a reaction gas which has been obtained by the catalytic oxidation of a compound selected from the group consisting of propylene, acrolein and mixtures thereof which process comprises: initially scrubbing said reaction gas which contains unreacted propylene and/or acrolein and impurities including water vapor, acetic acid, and formaldehyde countercurrently in an absorption column with a high boiling inert and extremely hydrophobic solvent selected from the group consisting of a hydrocarbon having a boiling point at standard pressure above 170°C and a viscosity within the temperature range of from 30° to 80°C of less than 10 centistokes, diphenyl ether, diphenyl and mixtures of the same to absorb acrylic acid from said reaction gas and to effect direct cooling of the reaction gas with said solvent; and thereafter recovering acrylic acid from said solvent by distillation and recycling said solvent to said absorption column.

2. A process as claimed in claim 1 wherein said countercurrent scrubbing is carried out with a mixture of diphenyl and diphenyl ether.

3. A process as claimed in claim 2 wherein said mixture comprises about 25% by weight of diphenyl and 75% by weight of said diphenyl ether.

4. A process as claimed in claim 2 wherein said countercurrent scrubbing is carried out at a temperature of from about 30° to 80° C.

5. A process as claimed in claim 1 wherein maleic anhydride is removed from said solvent by distillation after acrylic acid is removed and before the solvent is recycled to said absorption column.

6. A process as claimed in claim 1 wherein said absorbed acrylic acid and solvent is passed to a desorber column wherein said absorbed acrylic acid and solvent are contacted countercurrently with a stripping gas to remove residual water and minor amounts of acrolein, acetic acid and formaldehyde.

* * * * *